United States Patent
Biber

(10) Patent No.: US 12,392,514 B2
(45) Date of Patent: Aug. 19, 2025

(54) MAGNETIC RESONANCE SYSTEM WITH AIR SUCTION APPARATUS

(71) Applicant: Siemens Healthcare GmbH, Erlangen (DE)

(72) Inventor: Stephan Biber, Erlangen (DE)

(73) Assignee: Siemens Healthineers AG, Forchheim (DE)

(*) Notice: Subject to any disclaimer, the term of this patent is extended or adjusted under 35 U.S.C. 154(b) by 467 days.

(21) Appl. No.: 17/828,181

(22) Filed: May 31, 2022

(65) Prior Publication Data

US 2022/0397294 A1    Dec. 15, 2022

(30) Foreign Application Priority Data

Jun. 10, 2021 (DE) .................... 10 2021 205 906.6

(51) Int. Cl.
| | |
|---|---|
| A61B 5/00 | (2006.01) |
| A61B 5/055 | (2006.01) |
| F24F 11/00 | (2018.01) |
| F24F 13/02 | (2006.01) |
| F24F 8/10 | (2021.01) |

(52) U.S. Cl.
CPC .......... F24F 11/0001 (2013.01); A61B 5/055 (2013.01); A61B 5/704 (2013.01); F24F 13/0218 (2013.01); F24F 8/10 (2021.01)

(58) Field of Classification Search
CPC ...... F24F 11/0001; F24F 13/0218; F24F 8/10; A61B 5/055; A61B 5/704
USPC ....................................................... 454/284
See application file for complete search history.

(56) References Cited

U.S. PATENT DOCUMENTS

| | | |
|---|---|---|
| 2004/0255937 A1 | 12/2004 | Sun |
| 2016/0038101 A1 | 2/2016 | Benner et al. |
| 2021/0330413 A1* | 10/2021 | Feeley .............. A61B 46/23 |
| 2022/0054666 A1* | 2/2022 | Phillips ............. A61M 16/201 |

FOREIGN PATENT DOCUMENTS

| | | | |
|---|---|---|---|
| CN | 105361884 A | 3/2016 | |
| CN | 110006100 A | 7/2019 | |
| CN | 212439158 U | 2/2021 | |
| DE | 2503698 A1 | 8/1976 | |
| DE | 102014215544 A1 | 2/2016 | |
| DE | 202020103535 U1 | 7/2020 | |
| DE | 202020102737 U1 | 9/2020 | |
| EP | 3799784 A1 * | 4/2021 | ............. A61B 3/11 |

OTHER PUBLICATIONS

Claus, Leutkirch, DE202020102737 Translation.pdf, "Infektionsschutzvorrichtung zum Infektionsschutz von einer und/oder vor einer Person bzgl", Sep. 2020, pp. 1-15.*

* cited by examiner

Primary Examiner — Michael G Hoang
Assistant Examiner — Ryan L Faulkner
(74) Attorney, Agent, or Firm — Lempia Summerfield Katz LLC

(57) ABSTRACT

A magnetic resonance system has an air suction apparatus configured and arranged so as to suck air exhaled by a patient examined by the MR system. A method for operating the MR system is also provided, with which air exhaled by a patient examined by the MR system is sucked in.

16 Claims, 1 Drawing Sheet

1 MR system
2 MR device
3 Patient compartment
4 Patient table
5 Air suction apparatus
6 Air conveying facility
7 Filter apparatus
8 Air intake channel
9 Branch
10 Air intake opening
11 Shut-off valve
12 Head coil
13 Posterior part
14 Collar
15 Anterior part
16 Air suction channel
16a Anterior section
17a Coupling opening
17p Coupling opening
18 Air suction apparatus
K Head
N Nose
P Patient

MAGNETIC RESONANCE SYSTEM WITH AIR SUCTION APPARATUS

The present patent document claims the benefit of German Patent Application No. 10 2021 205 906.6, filed Jun. 10, 2021, which is hereby incorporated by reference in its entirety

TECHNICAL FIELD

A magnetic resonance (MR) system and a method for operating the MR system are disclosed.

BACKGROUND

In the context of the COVID-19 pandemic, new concepts for examinations in MR (magnetic resonance tomography) systems are required in the long term, which contribute to reducing a risk of infection by way of contact areas and particulate matter between the patient and operator and between two patients examined in succession.

Contact areas were previously cleaned using disinfectant detergent. The surfaces must be supplied (e.g., lacquered in the case of plastic surfaces) so that they prevent detergent from penetrating the plastic, for instance.

Active patient ventilation exists, which blows air through slots in the housing or in a body or local coil into the interior of a patient compartment of a stationary patient compartment (also referred to as "bore"). For the purpose of patient ventilation, a ventilation and thus cooling of the patient and odor problems is to be avoided between consecutive patients. This is particularly advantageous in the case of MR devices with a strong B0 field, e.g., of 3 tesla or more.

SUMMARY AND DESCRIPTION

The object of the present disclosure is to overcome the disadvantages of the prior art at least partially and in particular to provide an option for reducing a risk of infection as a result of airborne illnesses, (e.g., due to viruses and bacteria), during a MR examination.

The scope of the present disclosure is defined solely by the appended claims and is not affected to any degree by the statements within this summary. The present embodiments may obviate one or more of the drawbacks or limitations in the related art.

The object is achieved by a magnetic resonance (MR) system having an air suction apparatus, which is configured and arranged to suck air exhaled by a patient examined by the MR system.

This is advantageous in that air exhaled by a patient containing viruses and/or bacteria is not distributed or only distributed to a reduced degree in the MR device during a MR examination and is then also not able to accumulate, or only to a reduced degree, on surfaces of the MR device or other surfaces, such as a local coil and the patient table, but is instead sucked from the MR device. The sucked air may be released at a safe point and/or be treated in order to remove the harmful germs. Therefore, a spread of COVID-19 may be reduced, for instance, but is not restricted thereto.

As components, the MR system may have a stationary MR device (e.g., including one or more gradient coils, one or more transmitting antennas, and one or more receiving antennas), a patient table (which may also be referred to as patient couch), and possibly one or more local coils, (e.g., a head coil, a neck coil, etc.). MR systems are known in principle and are therefore not explained in more detail.

In one development, the air suction apparatus has at least one air conveying facility with a suction side and an outlet side, wherein at least one channel ("air intake channel") is connected to the suction side. One end of the air intake channel is therefore connected to the suction side of the air conveying facility, while the other end provides at least one air intake opening. Air exhaled by the patient is sucked or taken in by way of the at least one air intake opening, flows through the at least one air intake channel to the air conveying facility and is blown out again through the air conveying facility, possibly by way of an air outlet channel. At least one air intake channel may have one or more branches or branched channel sections, so that this air suction channel may have one end for connection with the air conveying facility and a plurality of air intake openings assigned to the respective branches. A channel section may also have a plurality of air intake openings. The air conveying facility may have at least one fan.

In one embodiment, the MR system has a MR head coil, wherein at least one air intake opening of the air suction apparatus or of the at least one air intake channel is arranged on the MR head coil. The advantage is achieved in that a particularly effective suction of the exhaled air is achieved, because the at least one air intake opening is located in proximity to the nose and mouth of the patient.

In one development, at least one air intake opening is arranged on a lower or inferior region of the MR head coil. This is advantageous in that the at least one air intake opening is located in a region which is under particular stress as a result of the exhaled air, because the mouth is located there and the air exhaled through the nose is also exhaled in this region, which permits an exceptionally effective suction of the exhaled air.

In one embodiment, the MR head coil has an anterior part (front part) (e.g., covering the front head half), a posterior part (rear part) (e.g., covering the rear head), and at least one air intake opening arranged on the anterior part. This advantageously likewise permits a particularly effective suction of the exhaled air, because this may be exhaled forward in respect of the head.

The at least one air intake opening of this at least one air intake channel is arranged, in particular, on an exterior of the anterior part or opens into a region on the anterior part.

With a MR examination using a head coil, the head of the patient may be placed in the posterior part of the head coil and then the anterior part of the head coil may be positioned, (e.g., inserted, snap-fitted, etc.) onto the posterior part.

In one embodiment, at least one air intake opening is integrated into the anterior part. This may be implemented, for instance, in that at least one air intake channel runs in the anterior part and one or, in the case of branching, a plurality of air intake openings opens into a surface of the anterior part.

Alternatively, at least one air intake channel may be pushed into corresponding cut-outs in the anterior part or fastened to at least one support of the anterior part from the outside.

In one development, at least one air intake opening, (e.g., all air intake openings), are arranged on an exterior of the anterior part. This is advantageous in that the patient only notices the intake air flow to a limited degree or practically not at all.

In an alternative or additional development, at least one air intake opening, (e.g., all air intake openings), is/are arranged on an exterior of the anterior part. This is advantageous in that the suction effect is particularly effective.

In one embodiment, at least one air intake channel runs in sections through the posterior part and in sections through the anterior part and posterior sections and anterior sections of the at least one air intake channel is connected to one another in an air-permeable manner when the anterior part is attached. This is advantageous in that no hindering tubes need to be placed from the anterior part between the anterior part and the air conveying facility but may be connected to the posterior part in a less hindering manner behind the patient. Instead, the at least one anterior section is connected to the at least one posterior section by direct insertion by way of corresponding coupling opening(s) or air interface (s), for instance. The direct insertion has the advantage that when the anterior part is placed on the posterior part, it automatically brings about an air coupling.

In one embodiment, the posterior sections and the anterior sections of the at least one air intake channel are connected to one another when the anterior part is put on a collar of the posterior part. This may also be seen that the posterior coupling opening(s) or air interface(s) are embedded into the collar of the posterior part. The advantage is achieved in that a particularly large installation space is made available and the course of the at least one posterior section of the air intake channel may be moved particularly without hindrance by other components of the posterior part. A further advantage of the transfer of the at least one channel section posterior part to the anterior part includes the associated at least one coupling opening being effectively usable as an air intake opening when the posterior part is not attached or not available. An air suction is therefore provided without further measures even when the anterior part is not available. This is particularly effective in the case of air exhaled from a patient's nose. To this end, it is particularly advantageous if a plurality of air channels is available, because a plurality of coupling openings is then also available. When the anterior part is attached, the coupling openings are sealed hereby, and the air is taken in through the air intake opening(s) in the anterior part.

In one embodiment, at least one air intake opening is arranged on a mouth/nose region of the anterior part. This enables a particularly effective suction of exhaled air.

In an alternative or additional embodiment, the air suction apparatus has at least one flexible air intake channel, which may be fastened to a patient table or to a local coil. The advantage is therefore achieved in that the head coil does not need to be adjusted or only marginally to the at least one air intake channel. Another advantage includes the possibility of an effective suction of exhaled air also being provided without the presence of an anterior part or also without head coils in a constructively simple manner. This embodiment has, as a further advantage, that it may be embodied to be especially independently manageable, which facilitates, e.g., a stowage and exchange and also a cleaning of the at least one air intake channel.

In one development, if the at least one flexible air intake channel may be fastened to a local coil, a mirror support of the local coil is additionally embodied as a support for the air intake channel. This advantageously produces a particularly compact arrangement and opening of the air intake channel (with one or more it is a development that air suction openings) in the mouth/nose region of the anterior part.

In one development, if the at least one flexible air intake channel may be fastened to a patient table, the at least one air intake channel may be fastened directly to the patient table.

In an alternative or additional embodiment, the MR system has a stationary MR device, wherein a number of air intake openings, of the air suction apparatus, distributed across a length of a patient compartment, open into the patient compartment. This is advantageous in that this achieves a reduction in concentration of bacteria and viruses or other germs in the patient compartment, namely also without parts of the air suction apparatus being accommodated in the patient compartment, e.g., as separate components or integrated into a local coil.

In one embodiment, the air intake openings may be selectively optionally air permeable and closeable as a function of a position of the patient, in particular his or her head, located in the patient compartment. As a result, air intake openings may advantageously be opened in a targeted manner in the vicinity of the head and air may thus be sucked from a spatial region of the patient compartment, in which the head lies, which enables a particularly effective suction of exhaled air. The information relating to the position of the patient, in particular his or her head, may be determined e.g., by the position of the patient table or by an image recognition.

In one embodiment, the air suction apparatus has at least one filter apparatus for filtering the suctioned air. The advantage is achieved in that the air output by the air suction apparatus has a lower quantity of germs.

In one embodiment, the filter apparatus is a replaceable filter apparatus. The ability to replace the at least one filter apparatus (including one or more filters for germs) allows for simple maintenance of a filter effectiveness.

In one development, the filter apparatus may have one or more filters which may be replaced by a service technician or a user of the MR system.

The filter apparatus may be arranged at any point in the air flow of the air suction apparatus, (e.g., on the local coil, on the patient table, and/or on the air conveying facility).

In one development, the filter apparatus may be monitored with respect to its state. If the state is no longer classified, an indication of a filter replacement may be output. The state may be correlated for instance with a useful life and/or an air flow throughput (e.g., accumulated air flow volume). Therefore, the replacement of the filter may be identified and an indication to replace the filter, after reaching or exceeding a predetermined threshold value of the useful life, and/or the accumulated air flow throughput or additionally or alternatively also based on other criteria, may be output.

In one embodiment, an air flow volume of the air suction apparatus may be set variably, e.g., by a user or operator of the MR system or automatically by the MR system. This provides a possibility of setting the air flow volume to a level which is agreeable to the patient.

In one development, the air conveying facility is only switched on or activated for its operation if on the suction side at least one air intake channel is connected with an air intake opening. The MR system may establish this, e.g., by way of a similar mechanism such as for identifying a local coil.

The object is also achieved by a method for operating a MR system, with which air exhaled by a patient examined by the MR system is sucked. The method may be embodied similarly to the MR system and produces the same advantages.

The above-described properties, features, and advantages of this disclosure and the manner in which these are achieved will become more clearly and easily intelligible in connection with the following description of exemplary embodiments, which are explained in further detail with reference to the drawings. For clarity of illustration identical elements, or elements having an identical effect, may be given identical reference characters.

DETAILED DESCRIPTION

Figure 1:
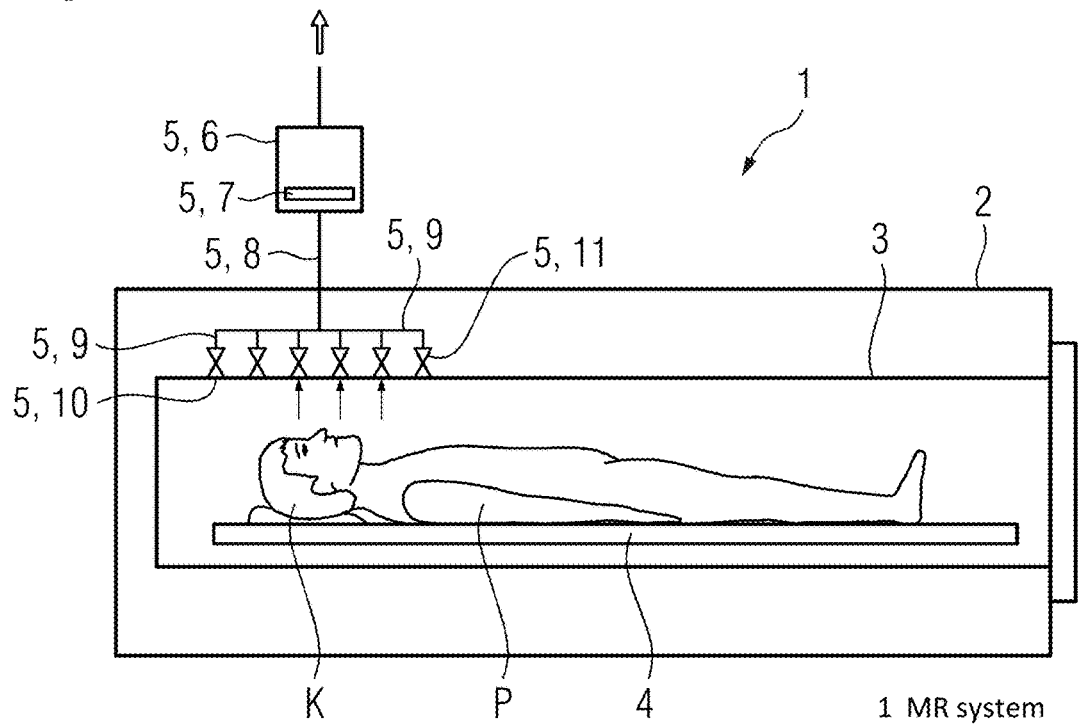
FIG. 1 depicts as a sectional representation in a side view a drawing of a MR system with a stationary MR device, according to an embodiment.

FIG. 1 depicts as a sectional representation in the side view a drawing of a MR system 1 with a stationary MR device 2, into the patient compartment 3 ("bore") of which a patient P lying on a patient table 4 has been inserted head K first. The design of the stationary MR device 2 with various coils etc. for carrying out a MR examination on the patient is essentially well-known. The MR system 1 further may have a control and evaluation console (above FIG.) on which an operator may control the MR device 2 and on which MR images may also be observed, for instance.

The MR system 1 additionally has an air suction apparatus 5, which is configured and arranged so as to suck air exhaled by a patient P examined by the MR device 2. This has an air conveying facility 6 on or, as shown, outside of the MR device 2, which for instance one or more fans (above FIG.) and a filter apparatus 7 for filtering germs out from the through-flowing air. The filtered air is output on the pressure side of the air conveying facility 6 and indicated in an exhaust air system or in the external air.

For instance, the power of the air conveying facility 6 and thus of the air volume flow conveyed through the air conveying facility 6 may be adjusted variably by way of the control console. An indication may also be output to the control console if one or more filters of the filter apparatus 7 are to be replaced.

An air intake channel 8 which splits into a number of branches 9 upstream of or, as shown, in the MR device 2, is connected on a suction side of the air conveying facility 6. Each of the branches 9 opens into a wall of the patient compartment 2 and therefore forms there a respective air intake opening 10. The branches 9 are shown here concentrated in the region of a head K of the patient P but may be distributed arbitrarily across the length of the patient compartment in respect of the location and number. The branches 9 and thus air intake openings 10 may also be distributed in the peripheral direction of the, in some cases, cylinder-shaped patient compartment 2, e.g., here in the peripheral direction about a longitudinal axis of the patient compartment 2 at sheet level.

Some or all of the branches 9 may be equipped with a respective shut-off valve 11, so that the associated air intake openings 10 may be selectively optionally air-permeable and closeable. An intake air flow in the patient compartment 2 may therefore be adjusted in a targeted manner to the patient P and to the exhaled air. For instance, the shut-off valves 11 of those branches 9 or air intake openings 10 may be opened selectively, which border a spatial region of the patient compartment 2, in which the highest concentration of exhaled air may be available, e.g., above (anterior) the mouth and below (inferior) the nose, as shown by the arrows. Other air suction openings may remain closed. The position of the head K may be derived, e.g., from the position of the patient table 4 in conjunction with the relative position of the patient P on the patient table 4 or from an image evaluation.

Figure 2:
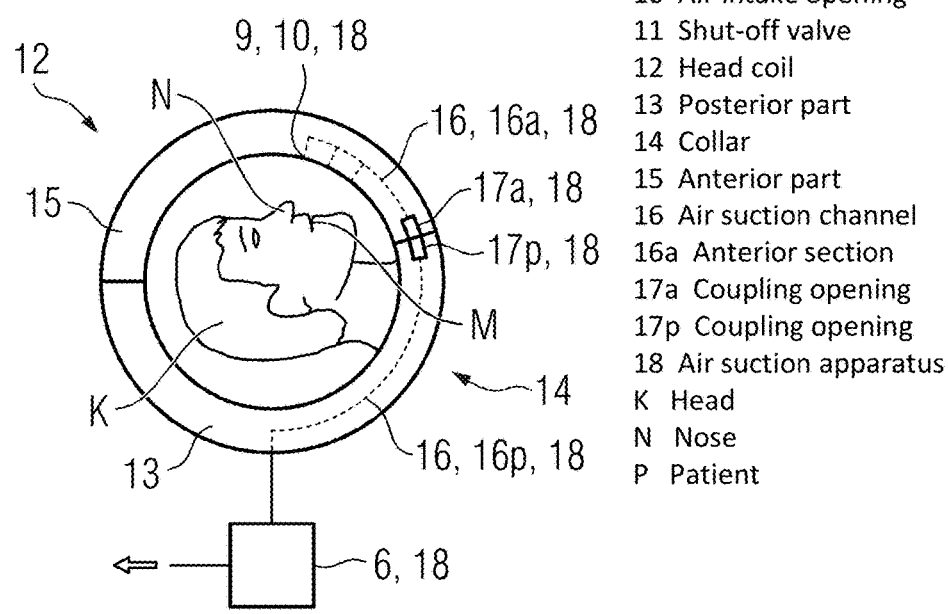
FIG. 2 depicts as a sectional representation in the side view a drawing of a head coil, according to an embodiment.

FIG. 2 depicts as a sectional representation in the side view a drawing of a local coil in the form of a head coil 12. This may represent a component of the MR system 1 and be used together with the MR device 2.

The head coil 12 has a posterior part 13, in which the head K of the patient P is placed. The inferior region of the posterior part 13 nestles around the neck of the patient and is therefore also referred to as a collar 14. The collar 14 is open on the anterior in order to be able to insert the neck. The anterior surface of the collar 14 is located inferior to a nose N of the patient P and thus in or slightly below a flow of breath exhaled through the nose N.

The head coil 12 further has an anterior part 15, which may be attached, in particular inserted, from the anterior side onto the posterior part 13, which anterior part 15 covers the face of the head K and thus also nose N and mouth M.

Here, a plurality of air intake openings 10, which forms open end faces of corresponding branches 9 of an "anterior" section 16a, running in the anterior part 15 of an air suction channel 16 integrated into the head coil 12 of an air suction apparatus 18, is located on an inner side of the anterior part 15, for instance. The air intake openings 10 are located anterior to the mouth M and inferior to the nose N and therefore lie in the flow of breath produced by the mouth M and nose N. The air intake openings 10 are therefore located on a mouth/nose region of the anterior part 15. Similar to FIG. 1, the air intake openings 10 may also be distributed in the peripheral direction about a horizontal axis lying at the sheet level.

The various branches 9 of the "anterior" section 16a converge to form one or more coupling openings 17a, which are present in a contact area, which is attached to a corresponding contact area in the collar 14 of the posterior part 13. When the anterior part is attached, the at least one coupling opening 17a is connected to at least one corresponding coupling opening 17p in the collar 14 of the posterior part 13 to form an air interface, in particular by a direct insertion. The at least one coupling opening 17p forms one end of at least one "posterior" section 16p of the air suction channel 16, which runs in the posterior part 13, which exits at the other side from the posterior part 13 and is connected to the suction side of an air conveying facility 6. The air conveying facility 6 may be the air conveying facility 6 shown in FIG. 1 or may be an air conveying facility 6 which differs therefrom.

If the air suction channel 16 is connected to the air conveying facility 6, an operator may switch on the air conveying facility 6 and may adjust the throughput air volume or rate of air flow. If the air conveying facility 6 is switched on, it sucks air through the air intake openings 10, through the anterior section 16a of the air intake channel 16, through the coupling openings 17a, 17p connected in an air-permeable manner with one another and through the posterior section 16p and to a suitable outlet region, e.g., after filtering. The at least one filter may be located at any point in the conveyed air flow.

If the anterior part 15 is alternatively removed, air is taken in through the coupling opening(s) 17p of the posterior part 13. As a result, at least the flow of breath exhaled through the nose N may be taken in.

Although the disclosure has been illustrated and described in detail by the exemplary embodiments shown, the disclosure is not restricted thereto, and other variations may be derived therefrom by a person skilled in the art without departing from the protective scope of the disclosure.

Therefore, with a MR examination, both air suction apparatuses 5 and 18 may be operated simultaneously by using a head coil 12.

In general, "a," "an," etc., may be understood as singular or plural, in particular in the sense of "at least one" or "one or more," etc., provided this is not explicitly excluded, e.g., by the expression "precisely one," etc.

A numerical value may also include the given value as well as a tolerance range, provided this is not explicitly excluded.

It is to be understood that the elements and features recited in the appended claims may be combined in different ways to produce new claims that likewise fall within the scope of the present disclosure. Thus, whereas the dependent claims appended below depend on only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A magnetic resonance (MR) system comprising:
   an air suction apparatus configured to suck air exhaled by a patient being examined by the MR system; and
   a stationary MR device having a patient compartment,
   wherein air intake openings of the air suction apparatus are distributed across a length of the patient compartment and open into the patient compartment,
   wherein each air intake opening of the air intake openings comprises a shut-off valve that is individually selectively air-permeable and closeable as a function of a position of a head of the patient located in the patient compartment, and
   wherein intake air flow into the air suction apparatus from the patient compartment is configured to be adjusted via closing or opening respective shut-off valves of the air intake openings based on the position of the head of the patient.

2. The MR system of claim 1, further comprising:
   a MR head coil,
   wherein the air suction apparatus further comprises at least one air intake opening arranged on the MR head coil.

3. The MR system of claim 2, wherein the air suction apparatus has at least one replaceable filter apparatus configured to filter intake air.

4. The MR system of claim 3, wherein an air flow volume of the air suction apparatus is configured to be adjusted variably.

5. The MR system of claim 2, wherein the MR head coil has an anterior part and a posterior part, and
   wherein an air intake opening of the at least one air intake opening is on the anterior part.

6. The MR system of claim 5, wherein the air intake opening is integrated into the anterior part.

7. The MR system of claim 5, wherein the air intake opening is arranged on a mouth/nose region of the anterior part.

8. The MR system of claim 1, wherein the air suction apparatus has at least one flexible air suction channel configured to be fastened to a patient table or to a local coil.

9. The MR system of claim 1, wherein the air suction apparatus has at least one replaceable filter apparatus configured to filter intake air.

10. The MR system of claim 9, wherein an air flow volume of the air suction apparatus is configured to be adjusted variably.

11. The MR system of claim 1, wherein the position of the head of the patient is configured to be derived from (i) a position of a patient table in conjunction with a relative position of the patient on the patient table or (ii) an image evaluation.

12. A magnetic resonance (MR) system comprising:
    an air suction apparatus configured to suck air exhaled by a patient being examined by the MR system; and
    a MR head coil having an anterior part and a posterior part,
    wherein an air intake opening of the air suction apparatus is arranged on the anterior part of the MR head coil,
    wherein at least one air intake channel having the air intake opening runs in sections through the posterior part and in sections through the anterior part, and
    wherein posterior sections and anterior sections of the at least one air intake channel are connected to one another in an air-permeable manner when the anterior part is attached.

13. The MR system of claim 12, wherein the posterior sections and the anterior sections of the at least one air intake channel are connected to one another when the anterior part is attached to a collar of the posterior part.

14. The MR system of claim 13, wherein the air intake opening is arranged on a mouth/nose region of the anterior part.

15. A method for operating a magnetic resonance (MR) system, the method comprising:
    providing a stationary MR device having a patient compartment, wherein air intake openings of an air suction apparatus of the MR system are distributed across a length of the patient compartment and open into the patient compartment, wherein each air intake opening of the air intake openings comprises a shut-off valve that is individually selectively air-permeable and closeable as a function of a position of a head of a patient located in the patient compartment;
    sucking in, by the air suction apparatus of the MR system, air exhaled by the patient being examined by the MR system; and
    adjusting intake air flow into the air suction apparatus from the patient compartment via closing or opening respective shut-off valves of the air intake openings based on the position of the head of the patient.

16. The method of claim 15, further comprising:
    deriving the position of the head of the patient from a position of a patient table in conjunction with a relative position of the patient on the patient table; or
    deriving the position of the head of the patient from an image evaluation.

* * * * *